(12) United States Patent
Valentine, Jr. et al.

(10) Patent No.: US 12,343,016 B2
(45) Date of Patent: Jul. 1, 2025

(54) HANDHELD ELECTROMECHANICAL SURGICAL SYSTEM

(71) Applicant: Covidien LP, Mansfield, MA (US)

(72) Inventors: David E. Valentine, Jr., Hamden, CT (US); Charles R. Kollar, Washington, DC (US); Alexander J. Hart, Tolland, CT (US); James P. Delbo, Danville, PA (US); Haley E. Strassner, Hamden, CT (US)

(73) Assignee: Covidien LP, Mansfield, MA (US)

( * ) Notice: Subject to any disclaimer, the term of this patent is extended or adjusted under 35 U.S.C. 154(b) by 20 days.

(21) Appl. No.: 18/266,185

(22) PCT Filed: Dec. 3, 2021

(86) PCT No.: PCT/US2021/061773
§ 371 (c)(1),
(2) Date: Jun. 8, 2023

(87) PCT Pub. No.: WO2022/125390
PCT Pub. Date: Jun. 16, 2022

(65) Prior Publication Data
US 2024/0032929 A1    Feb. 1, 2024

Related U.S. Application Data

(60) Provisional application No. 63/122,539, filed on Dec. 8, 2020.

(51) Int. Cl.
*A61B 17/068* (2006.01)
*A61B 17/115* (2006.01)
*A61B 17/00* (2006.01)

(52) U.S. Cl.
CPC . *A61B 17/1155* (2013.01); *A61B 2017/00017* (2013.01); *A61B 2017/00398* (2013.01)

(58) Field of Classification Search
CPC . A61B 17/1155; A61B 17/068; A61B 17/072; B61B 17/1155; B61B 17/068; B61B 17/072
See application file for complete search history.

(56) References Cited

U.S. PATENT DOCUMENTS

| | | | | |
|---|---|---|---|---|
| 7,798,386 B2 * | 9/2010 | Schall | | A61B 17/07207 |
| | | | | 227/176.1 |
| 8,646,674 B2 * | 2/2014 | Schulte | | A61B 17/00491 |
| | | | | 623/23.72 |

(Continued)

FOREIGN PATENT DOCUMENTS

| EP | 3403591 A1 | 11/2018 |
|---|---|---|
| EP | 3506278 A1 | 7/2019 |
| WO | 2020014056 A1 | 1/2020 |

OTHER PUBLICATIONS

International Search Report for Application No. PCT/US2021/061773 dated Nov. 3, 2022.

(Continued)

*Primary Examiner* — Gloria R Weeks

(57) ABSTRACT

A surgical device includes a handle assembly having a power source, a motor coupled to the power source, and a controller configured to control the motor. The device also includes an adapter assembly configured to selectively couple to the handle assembly, the adapter assembly including a stapling transmission assembly movable by the motor. The device also includes a reload configured to selectively couple to a distal portion of the adapter assembly, the reload including a plurality of staples ejectable from the reload by the stapling transmission assembly. The device also includes an anvil assembly selectively couplable to the distal portion of the adapter assembly, the anvil assembly being movable relative to the reload, where the controller may be further configured to control the motor to move the stapling trans- (Continued)

mission assembly to eject the staples while compensating for mechanical losses of the stapling transmission assembly.

19 Claims, 10 Drawing Sheets

(56) References Cited

U.S. PATENT DOCUMENTS

| | | | | |
|---|---|---|---|---|
| 10,327,779 | B2* | 6/2019 | Richard | A61B 17/1155 |
| 10,478,189 | B2* | 11/2019 | Bear | A61B 17/1155 |
| 11,446,037 | B2* | 9/2022 | Kollar | G16H 40/40 |
| 12,064,107 | B2* | 8/2024 | Parks | A61B 17/0686 |
| 2016/0249945 | A1* | 9/2016 | Shelton, IV | A61B 17/115 |
| | | | | 606/171 |
| 2016/0374672 | A1* | 12/2016 | Bear | H02J 7/00 |
| | | | | 606/219 |
| 2016/0374673 | A1* | 12/2016 | Stager | A61B 17/1155 |
| | | | | 227/176.1 |
| 2017/0296213 | A1* | 10/2017 | Swensgard | A61B 17/32 |
| 2018/0353186 | A1* | 12/2018 | Mozdzierz | A61B 17/072 |
| 2019/0200998 | A1 | 7/2019 | Shelton, IV et al. | |
| 2020/0367891 | A1* | 11/2020 | Kollar | A61B 17/1155 |

OTHER PUBLICATIONS

Written Opinion for Application No. PCT/US2021/061773 dated Nov. 3, 2022.

* cited by examiner

HANDHELD ELECTROMECHANICAL SURGICAL SYSTEM

CROSS-REFERENCE TO RELATED APPLICATIONS

This application claims the benefit of U.S. Provisional Patent Application No. 63/122,539, filed Dec. 8, 2020, the entire contents of which are incorporated by reference herein.

BACKGROUND

1. Technical Field

The present disclosure relates to surgical devices. More specifically, the present disclosure relates to handheld electromechanical surgical systems for performing surgical procedures.

2. Background of Related Art

One type of surgical device is a circular clamping, cutting and stapling device. Circular staplers are used in a surgical procedure to reattach rectum portions that were previously transected, or similar procedures. Conventional circular clamping, cutting and stapling instruments include a pistol or linear grip-styled structure having an elongated shaft extending therefrom and a staple cartridge supported on the distal end of the elongated shaft. In this instance, a physician may insert an anvil assembly of the circular stapling instrument into a rectum of a patient and maneuver the anvil assembly up the colonic tract of the patient toward the transected rectum portions. The physician may also insert the remainder of the circular stapling instrument (including the cartridge assembly) through an incision and toward the transected rectum portions. The anvil and cartridge assemblies are approximated toward one another and staples are ejected from the cartridge assembly toward the anvil assembly to form the staples in tissue to affect an end-to-end anastomosis, and an annular knife is fired to core a portion of the clamped tissue portions. After the end-to-end anastomosis has been effected, the circular stapling apparatus is removed from the surgical site.

A number of surgical device manufacturers have developed product lines with proprietary powered drive systems for operating and/or manipulating the surgical device. In many instances the surgical devices include a powered handle assembly and an adapter assembly, which are reusable, and a disposable staple cartridge assembly that is selectively connected to the adapter assembly prior to use.

The adapter assembly includes multiple transmission assemblies, e.g., drive shafts, which transmit actuation from the powered handle to the disposable staple cartridge. During actuation, the transmission assemblies do not fully transmit actuation forces, which results in inaccurate actuation of the staple cartridge. Thus, there is a need for a system and method to compensate for such losses to ensure proper and accurate actuation of the staple cartridge.

SUMMARY

A powered circular stapler according to the present disclosure includes an outer shell housing, a power handle, an adapter assembly, and an end effector having a stapler reload and an anvil assembly. The shell housing and the end effector are single use components. The power handle and the adapter assembly are multi-procedure components, which are reprocessed between procedures.

The powered circular stapler is configured to determine position output from the encoders on the motor. However, this feedback does not account for the dynamic losses of the transmission assembly disposed in the adapter assembly used to eject staplers from the reload. In order to account for this dynamic loss, the adapter assembly, including the transmission assembly is run through an end of line final functional test where the stroke loss characteristics are mapped in terms of a second order equation and specific coefficient, which is stored in a storage device of the adapter assembly.

When the powered circular stapler starts to staple and cut, a controller of the power handle monitors the force from a strain gauge disposed in the adapter assembly. Using the coefficients that were stored in the storage device of the adapter assembly by the final functional tester, the controller calculates the stroke losses in real time. The controller then adds additional motor ticks (i.e., revolutions) in order to compensate for the strokes lost between a distal end of the transmission assembly engaging the reload and a proximal end of the transmission assembly coupled to a motor of the power handle. Since the controller monitors the strain gauge in real time, the controller continuously adjusts the motors output until a distal pusher of the transmission assembly achieves the target stroke.

According to one embodiment of the present disclosure a surgical device includes a handle assembly having a power source, a motor coupled to the power source, and a controller configured to control the motor. The device also includes an adapter assembly configured to selectively couple to the handle assembly, the adapter assembly including a stapling transmission assembly movable by the motor. The device also includes a reload configured to selectively couple to a distal portion of the adapter assembly, the reload including a plurality of staples ejectable from the reload by the stapling transmission assembly. The device also includes an anvil assembly selectively couplable to the distal portion of the adapter assembly, the anvil assembly being movable relative to the reload, where the controller may be further configured to control the motor to move the stapling transmission assembly to eject the staples while compensating for mechanical losses of the stapling transmission assembly.

Implementations of the above embodiment may include one or more of the following features. The surgical device where the stapling transmission assembly includes a pair of opposing flexible bands that deflect in response to compression resulting in the mechanical losses. The handle assembly further includes an encoder coupled to the motor. The controller may be further configured to calculate a distance traveled by the stapling transmission assembly. Adapter assembly includes a strain gauge assembly configured to measure force imparted on at least one of the stapling transmission assembly or the adapter assembly. The controller may be further configured to calculate a difference between two measurements and perform a comparison of the difference to a threshold delta force. The controller may be further configured to increment a total lost turns counter based on the comparison. The controller may be further configured to multiply the total lost turns counter by a force factor associated with the reload to determine an adjusted lost turns value. The controller may be further configured to increment the motor by the adjusted lost turns value.

According to another embodiment of the present disclosure a surgical device includes a handle assembly having: a power source, a motor coupled to the power source, and a controller configured to control the motor. The device also includes an adapter assembly configured to selectively couple to the handle assembly, the adapter assembly including a stapling transmission assembly movable by the motor, the stapling transmission assembly includes a pair of opposing flexible bands. The device also includes a reload configured to selectively couple to a distal portion of the adapter assembly, the reload including a plurality of staples ejectable from the reload by the stapling transmission assembly. The device also includes an anvil assembly selectively couplable to the distal portion of the adapter assembly, the anvil assembly being movable relative to the reload, where the controller may be further configured to control the motor to move the stapling transmission assembly to eject the staples while compensating for mechanical losses due to deflection of the opposing flexible bands in response.

Implementations of the above embodiment may include one or more of the following features. The surgical device where the handle assembly further includes an encoder coupled to the motor. The controller may be further configured to calculate a distance traveled by the stapling transmission assembly. Adapter assembly includes a strain gauge assembly configured to measure force imparted on at least one of the stapling transmission assembly or the adapter assembly. The controller may be further configured to calculate a difference between two measurements and perform a comparison of the difference to a threshold delta force. The controller may be further configured to increment a total lost turns counter based on the comparison. The reload includes a storage device storing a force factor and a plurality of coefficients. The controller may be further configured to multiply the total lost turns counter by a force factor associated with the reload to determine an adjusted lost turns value. The controller may be further configured to increment the motor by the adjusted lost turns value. The controller may be further configured to increment the total lost turns counter based on a second order equation including the coefficients and measured force. The reload and the anvil assembly are circular.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
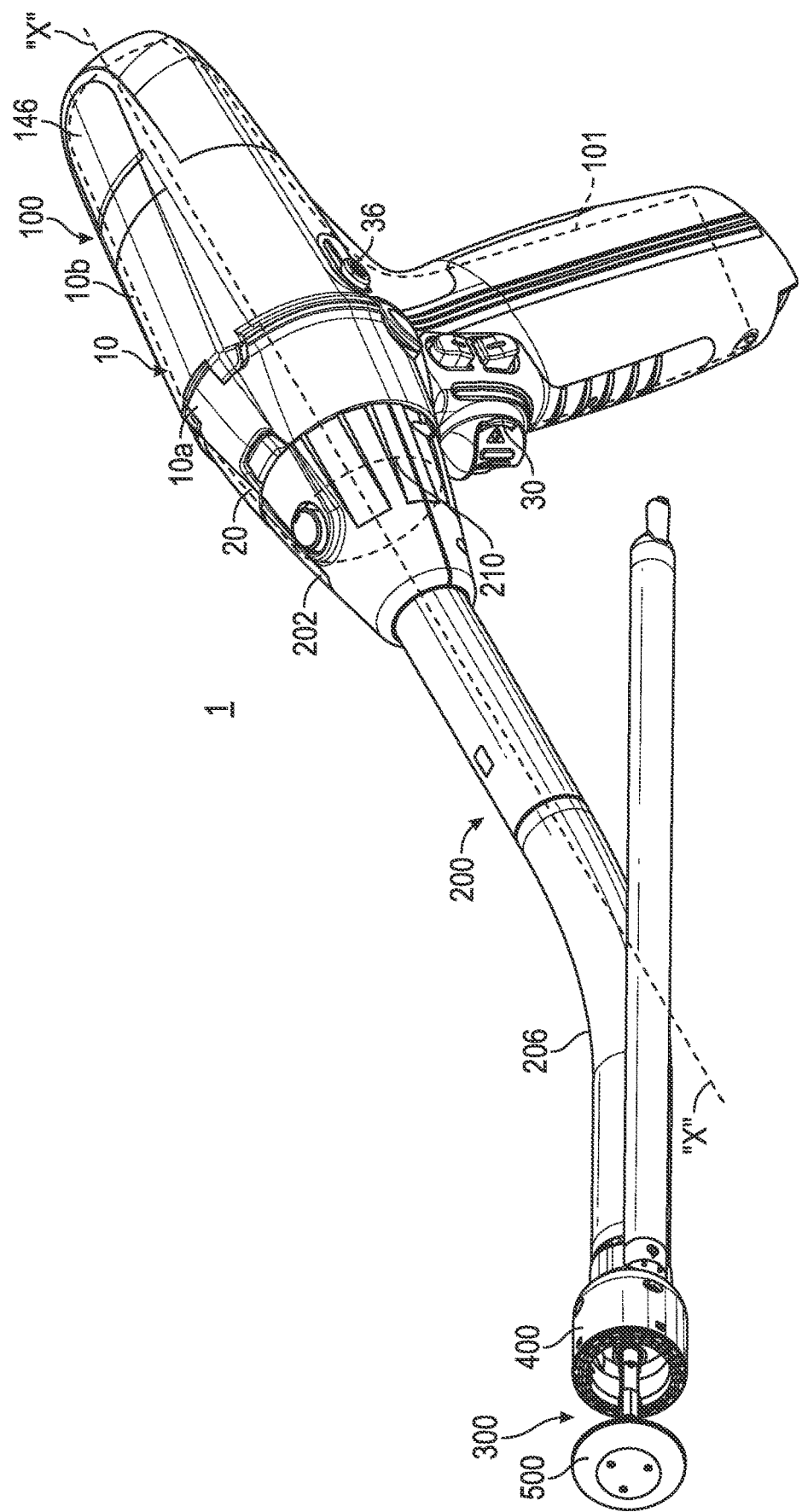
FIG. 1 is a perspective view of a handheld surgical instrument including a handle assembly, an adapter assembly, and an end effector, according to an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

The present disclosure provides a powered circular stapler 1 having a handle assembly, an adapter assembly coupled to the handle assembly, and an end effector coupled to the adapter assembly. The stapler allows for full, independent control of three functions: clamping, stapling, and cutting. This allows certain portions of the stapler to adapt if the tissue presents a non-ideal situation.

FIG. 1 illustrates a surgical device, such as, for example, a powered circular stapler 1 for forming end-to-end anastomosis ("EEA"), including a handle assembly 100, which is configured for selective connection with an adapter assembly 200. The adapter assembly 200 is configured for selective connection with an end effector 300, which includes a reload 400 and an anvil assembly 500. The end effector 300 is configured to produce a surgical effect on tissue of a patient, namely, forming an anastomosis by connecting two portions of a structure (e.g., intestine, colon, etc.) by clamping, stapling, and cutting tissue grasped within the end effector 300.

The handle assembly 100 includes a power handle 101 and an outer shell housing configured to selectively receive and encase power handle 101. The shell housing 10 includes a distal half-section 10a and a proximal half-section 10b pivotably connected to distal half-section 10a. When joined, distal and proximal half-sections 10a, 10b define a shell cavity therein in which power handle 101 is disposed.

Distal and proximal half-sections 10a, 10b of shell housing 10 are divided along a plane that traverses a longitudinal axis "X" of adapter assembly 200. Distal half-section 10a of shell housing 10 defines a connecting portion 20 configured to accept a corresponding drive coupling assembly 210 (FIG. 3) of adapter assembly 200. Distal half-section 10a of shell housing 10 supports a toggle control button 30. Toggle control button 30 is capable of being actuated in four directions (e.g., a left, right, up and down).

Figure 2:
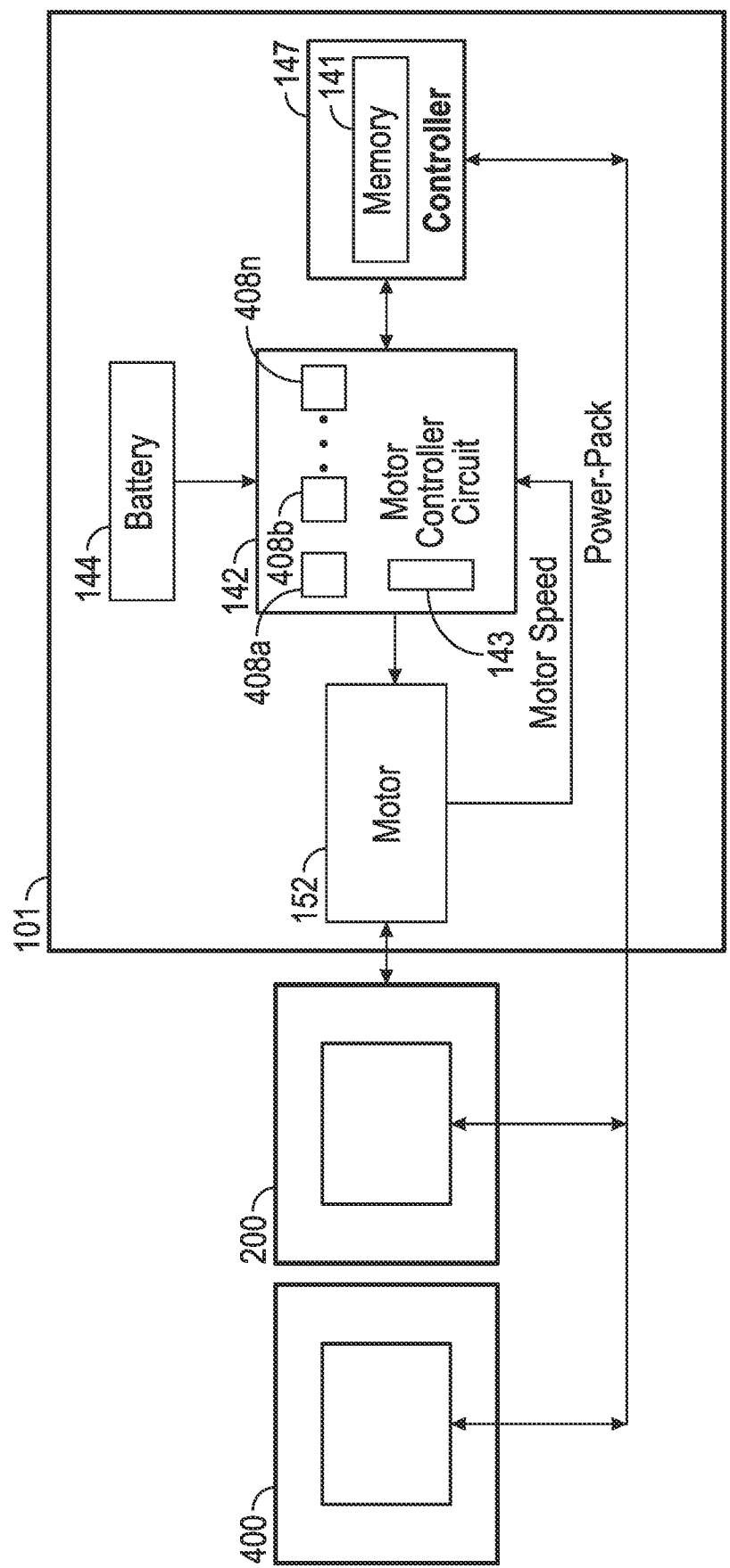
FIG. 2 is a schematic diagram of the handle assembly, the adapter assembly, and the end effector of FIG. 1.

With reference to FIGS. 1 and 2, the power handle 101 includes a main controller circuit board 142, a rechargeable battery 144 configured to supply power to any of the electrical components of handle assembly 100, and a plurality of motors 152 coupled to the battery 144. The power handle 101 also includes a display 146. In embodiments, the motors 152 may be coupled to any suitable power source configured to provide electrical energy to the motor 152, such as an AC/DC transformer. Each of the motors 152 is coupled a motor controller 143 which controls the operation of the corresponding motor 152 including the flow of electrical energy from the battery 144 to the motor 152. A main controller 147 is provided that controls the power handle 101. The main controller 147 is configured to execute software instructions embodying algorithms disclosed herein, such as clamping, stapling, and cutting algorithms which control operation of the power handle 101.

The motor controller 143 includes a plurality of sensors 408a . . . 408n configured to measure operational states of the motor 152 and the battery 144. The sensors 408a-n include a strain gauge 408b and may also include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motor 152. The sensor 408a also includes an encoder configured to count revolutions or other indicators of the motor 152, which is then use by the main controller 147 to calculate linear movement of components movable by the motor 152. Angular velocity may be determined by measuring the rotation of the motor 152 or a drive shaft (not shown) coupled thereto and rotatable by the motor 152. The position of various axially movable drive shafts may also be determined by using various linear sensors disposed in or in proximity to the shafts or extrapolated from the RPM measurements. In embodiments, torque may be calculated based on the regulated current draw of the motor 152 at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the adapter assembly 200 and/or the end effector 300 by counting revolutions of the motor 152.

The motor controller 143 is coupled to the main controller 147, which includes a plurality of inputs and outputs for interfacing with the motor controller 143. In particular, the main controller 147 receives measured sensor signals from the motor controller 143 regarding operational status of the motor 152 and the battery 144 and, in turn, outputs control signals to the motor controller 143 to control the operation of the motor 152 based on the sensor readings and specific algorithm instructions. The main controller 147 is also configured to accept a plurality of user inputs from a user interface (e.g., switches, buttons, touch screen, etc. coupled to the main controller 147).

The main controller 147 is also coupled to a memory 141. The memory 141 may include volatile (e.g., RAM) and non-volatile storage configured to store data, including software instructions for operating the power handle 101. The main controller 147 is also coupled to the strain gauge 408b of the adapter assembly 200 using a wired or a wireless connection and is configured to receive strain measurements from the strain gauge 408b which are used during operation of the power handle 101.

The power handle 101 includes a plurality of motors 152 each including a respective motor shaft (not explicitly shown) extending therefrom and configured to drive a respective transmission assembly. Rotation of the motor shafts by the respective motors function to drive shafts and/or gear components of adapter assembly 200 in order to perform the various operations of handle assembly 100. In particular, motors 152 of power handle 101 are configured to drive shafts and/or gear components of adapter assembly 200 in order to selectively extend/retract a trocar member 274 (FIG. 4) of a trocar assembly 270 of adapter assembly 200. Extension/retraction of the trocar member 274 opens/closes end effector 300 (when anvil assembly 500 is connected to trocar member 274 of trocar assembly 270), fire an annular array of staples 423 of reload 400, and move an annular knife (not explicitly shown) of reload 400.

The reload 400 includes a storage device 402 configured to store operating parameters of the reload 400 including starting clamping force, maximum clamping force, a force factor, and the like. Each type of reload 400 may have a corresponding starting clamping force, which the main controller 147 may obtain automatically by reading the starting clamping force value from the storage device 402 and/or set manually by the user by selecting either the type of the reload 400 or the clamping force directly. Starting clamping force may be any suitable threshold from about 100 pounds to about 200 pounds, in embodiments, the target clamping force may be approximately 150 pounds. In embodiments, a 33 mm sized reload 400 may have a clamping force of about 150 lbs.

Figure 3:
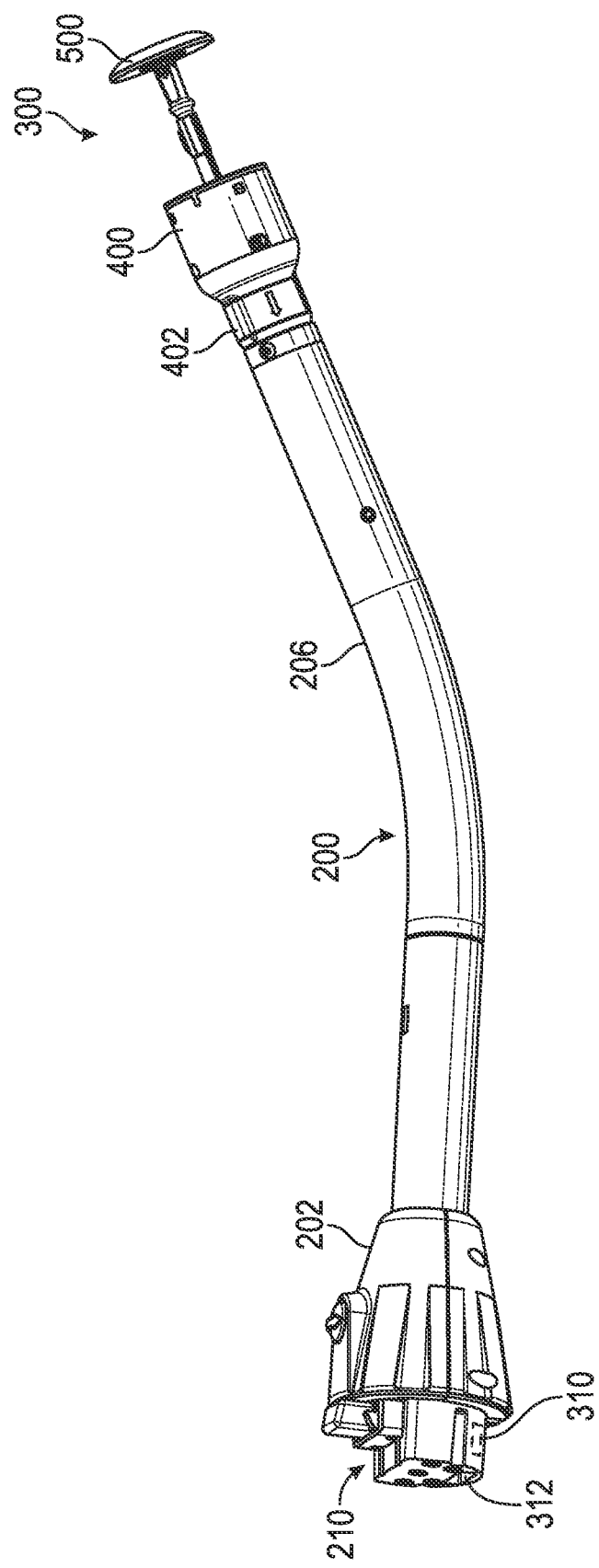
FIG. 3 is a side perspective view of the adapter assembly and the end effector, an annular reload and an anvil assembly, attached to the adapter assembly of FIG. 1 according to an embodiment of the present disclosure.
Figure 4:
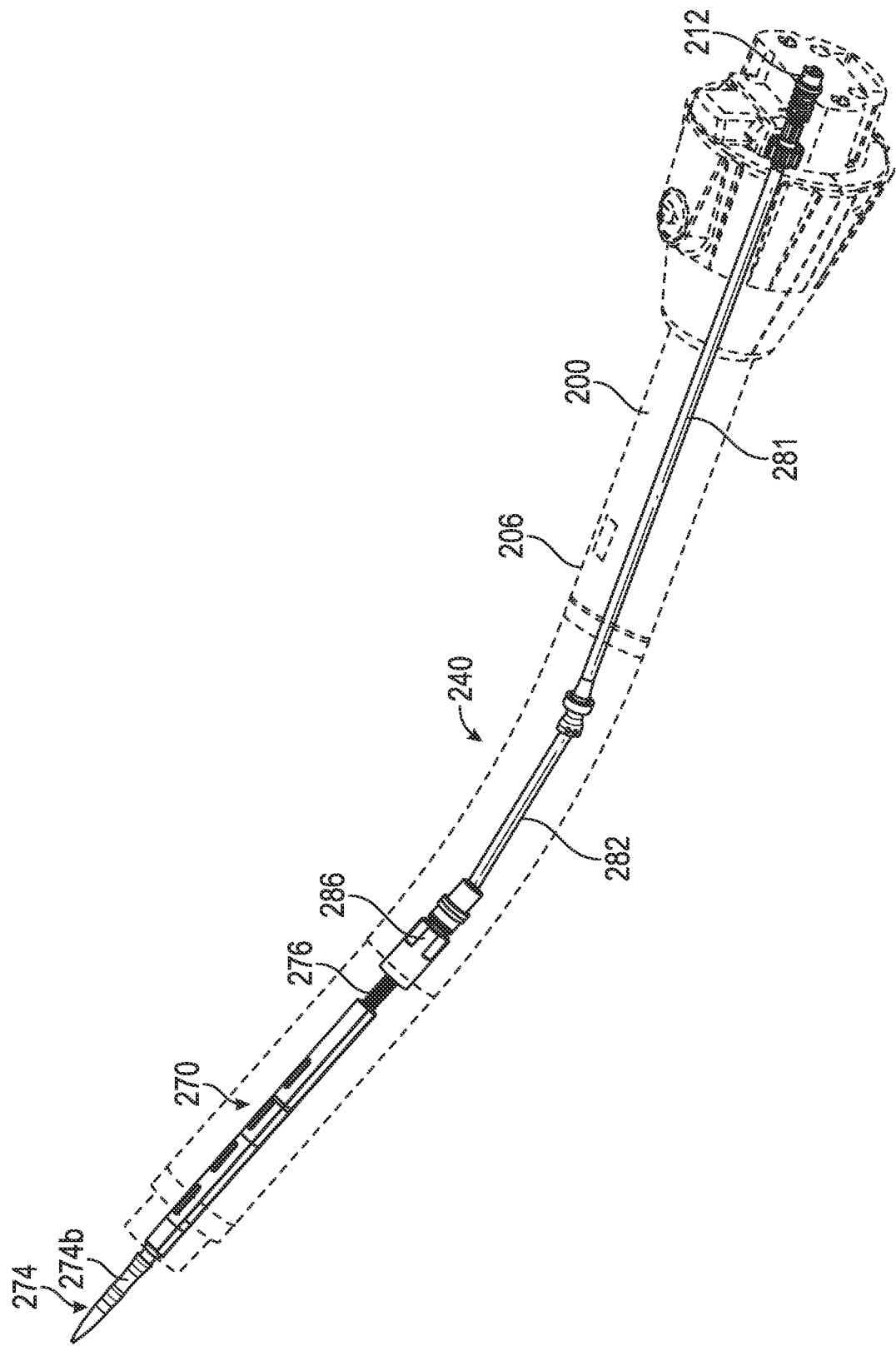
FIG. 4 is a perspective view of a clamping transmission assembly disposed within the adapter assembly of FIG. 1, shown partially in phantom.

Turning now to FIGS. 3 and 4, adapter assembly 200 includes an outer knob housing 202 and an outer tube 206 extending from a distal end of knob housing 202. Knob housing 202 and outer tube 206 are configured and dimensioned to house the components of adapter assembly 200. The knob housing 202 includes an electrical connector 312 and a storage device 310 coupled thereto. The storage device 310 is configured to store various operating parameters pertaining to the adapter assembly 200. Adapter assembly 200 is configured to convert rotation of coupling shafts (not explicitly shown) of handle assembly 100 into axial translations useful for operating trocar assembly 270 of adapter assembly 200, anvil assembly 500, and/or staple driver 430 or knife assembly (not explicitly shown) of reload 400.

Adapter assembly 200 further includes the trocar assembly 270 removably supported in a distal end of outer tube 206. Trocar assembly 270 includes a trocar member 274 and a drive screw 276 operably received within trocar member 274 for axially moving trocar member 274 relative to outer tube 206. A distal end 274b of trocar member 274 is configured to selectively engage anvil assembly 500, such that axial movement of trocar member 274, via a rotation of drive screw 276, results in a concomitant axial movement of anvil assembly 500.

With reference to FIG. 4, a clamping transmission assembly 240 includes first rotatable proximal drive shaft 212 coupled to one of the motors 152, a second rotatable proximal drive shaft 281, a rotatable distal drive shaft 282, and a coupling member 286, each of which are supported within the outer tube 206 of adapter assembly 200. Clamping transmission assembly 240 functions to extend/retract trocar member 274 of trocar assembly 270 of adapter assembly 200, and to open/close the anvil assembly 510 when anvil assembly 510 is connected to trocar member 274.

Figure 5:
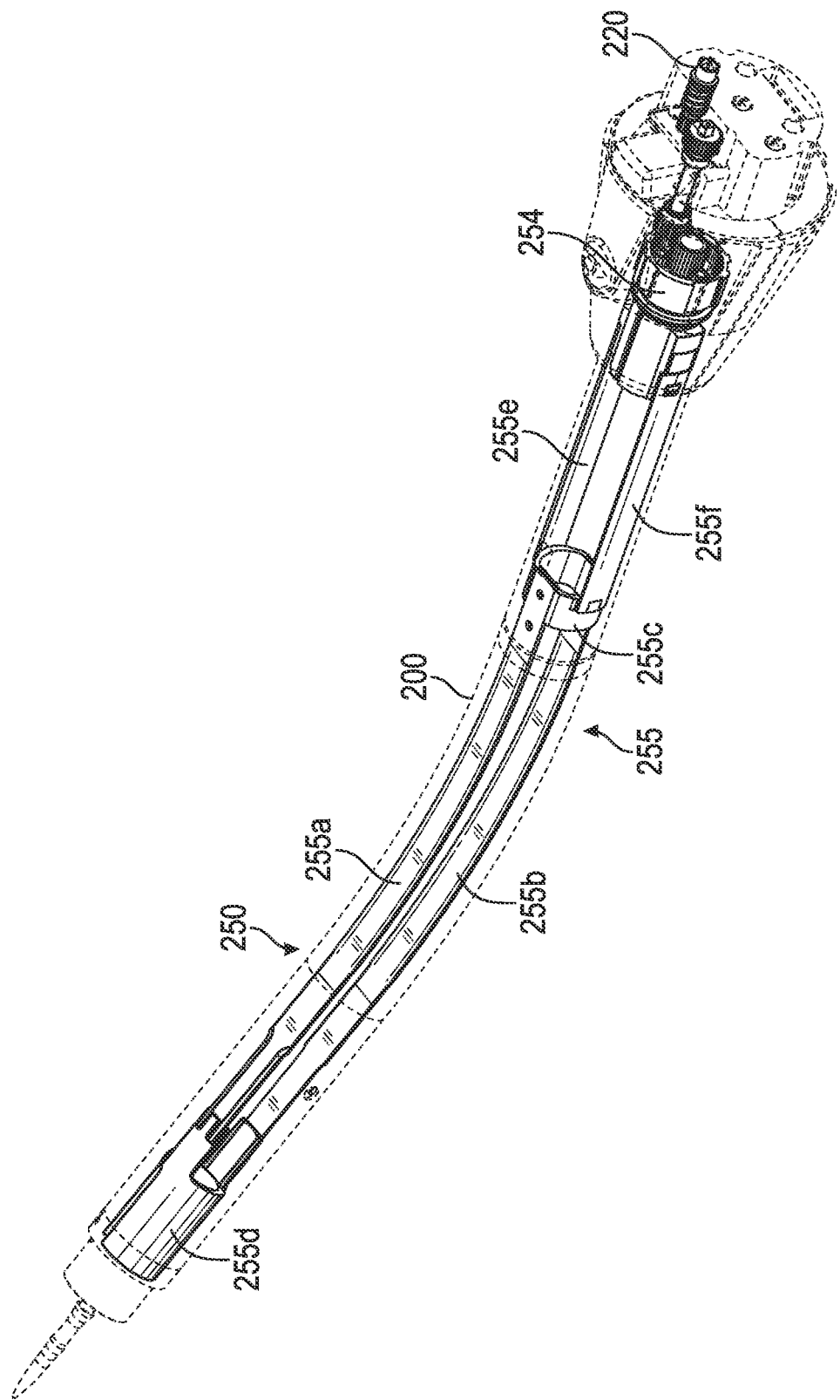
FIG. 5 is a perspective view of a stapling transmission assembly disposed within the adapter assembly of FIG. 1, shown partially in phantom.

With reference to FIG. 5, the adapter assembly 200 includes a stapling transmission assembly 250 for interconnecting one of the motors 152 and a second axially translatable drive member of reload 400, wherein the stapling transmission assembly 250 converts and transmits a rotation of one of the motors 152 to an axial translation of an outer flexible band assembly 255 of adapter assembly 200, and in turn, the staple driver 430 of reload 400 to fire staples 423 from the reload 400 and against anvil assembly 510.

The stapling transmission assembly 250 of adapter assembly 200 includes the outer flexible band assembly 255 secured to staple driver coupler 254. A second rotatable proximal drive shaft 220 is coupled to one of the motors 152 and is configured to actuate that staple driver coupler 254, which converts rotational movement into longitudinal movement. Outer flexible band assembly 255 includes first and second flexible bands 255a, 255b laterally spaced and connected at proximal ends thereof to a support ring 255c and at distal ends thereof to a proximal end of a distal pusher 255d. Each of first and second flexible bands 255a, 255b is attached to support ring 255c and distal pusher 255d. Outer flexible band assembly 255 further includes first and second connection extensions 255e, 255f extending proximally from support ring 255c. First and second connection extensions 255e, 255f are configured to operably connect outer flexible band assembly 255 to staple driver coupler 254 of stapling transmission assembly 250.

Figure 6:
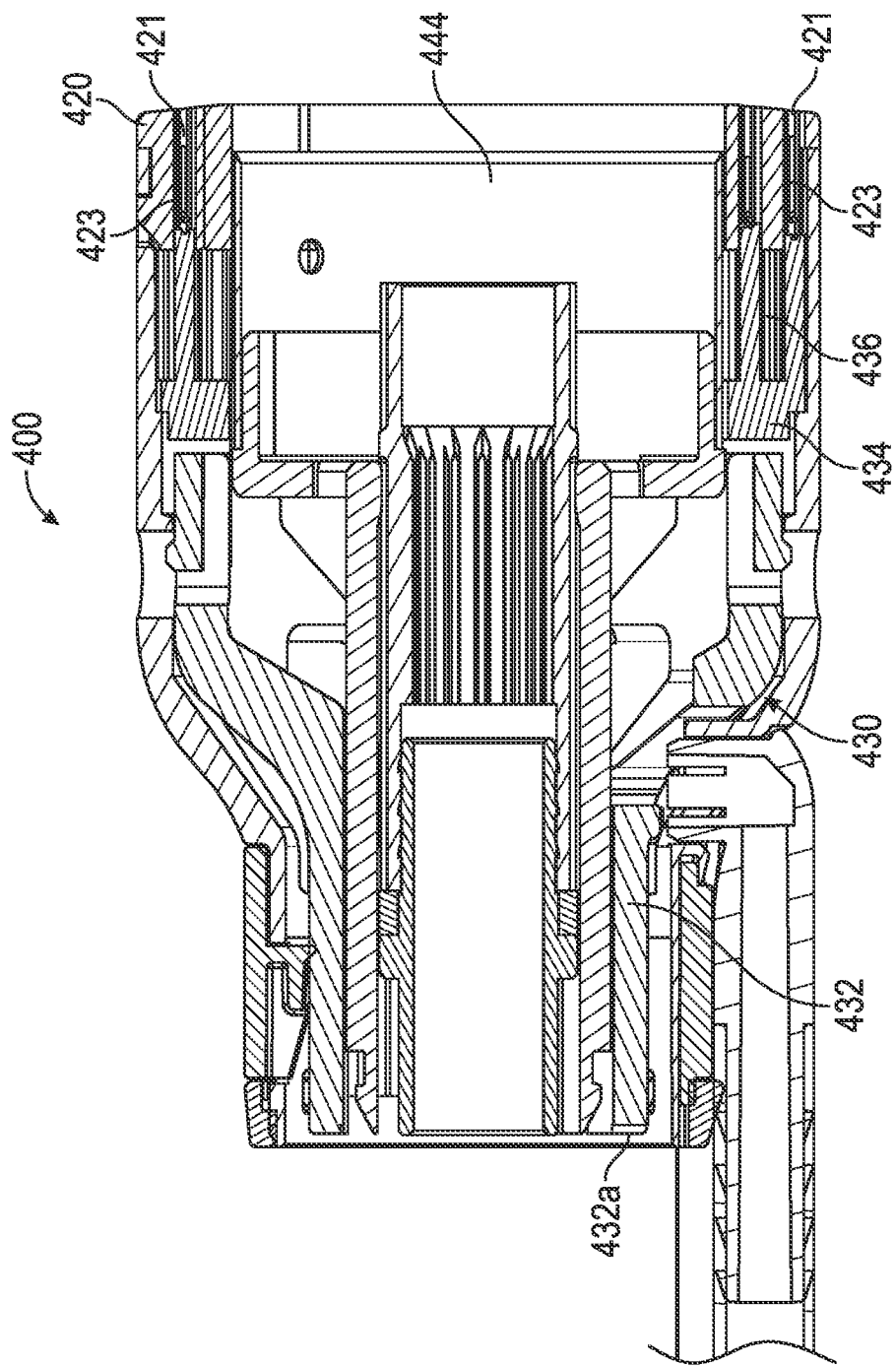
FIG. 6 is a cross-sectional view of a reload of the end effector of FIG. 1.

With reference to FIG. 6, staple driver 430 of reload 400 includes a staple cartridge 420 having a driver adapter 432 and a driver 434. A proximal end 432a of driver adapter 432 is configured for selective contact and abutment with distal pusher 255d of outer flexible band assembly 255 of stapling transmission assembly 250 of adapter assembly 200. In operation, during distal advancement of outer flexible band assembly 255, as described above, distal pusher 255d of outer flexible band assembly 255 contacts proximal end 432a of driver adapter 432 to advance driver adapter 432 and driver 434 from a first or proximal position to a second or distal position. Driver 434 includes a plurality of driver members 436 aligned with staple pockets 421 of staple cartridge 420 for contact with staples 423. Accordingly, advancement of driver 434 relative to staple cartridge 420 causes ejection of the staples 423 from staple cartridge 420.

Forces during an actuation of trocar member 274, closing of end effector 300 (e.g., a retraction of anvil assembly 500 relative to reload 400), and ejecting staples 423 from the reload 400 may be measured by the strain gauge 408b in order to monitor and control various processes, such as firing of staples 423 from reload 400; monitor forces during a firing and formation of the staples 423 as the staples 423 are being ejected from reload 400; optimize formation of the staples 423 (e.g., staple crimp height) as the staples 423 are being ejected from reload 400 for different indications of tissue; and monitor and control a firing of the annular knife of reload 400.

Figure 7:
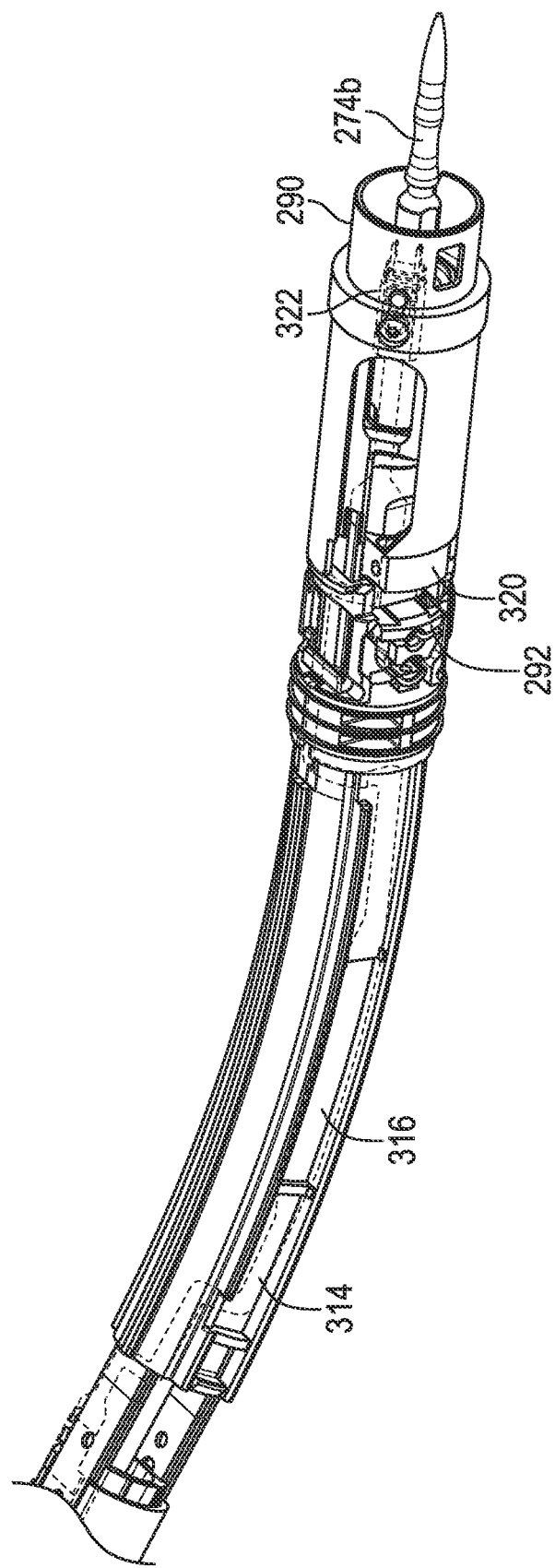
FIG. 7 is a perspective view of the adapter assembly, shown partially disassembled, with a strain gauge assembly.

With reference to FIG. 7, the strain gauge 408b of adapter assembly 200 is disposed within a strain gauge housing 320. The strain gauge 408b measures and monitors the retraction of trocar member 274 as well as the ejection and formation of the staples 423 from the reload 400. During the closing of end effector 300, when anvil assembly 500 contacts tissue, an obstruction, a tissue-contacting surface of the reload 400, staple ejection, or the like, a reaction force is exerted on anvil assembly 500 which is in a generally distal direction. This distally directed reaction force is communicated from anvil assembly 500 to the strain gauge 408b. The strain gauge 408b then communicates signals to main controller circuit board 142 of power handle 101 of handle assembly 100. Graphics (FIG. 8) are then displayed on the display 146 of handle assembly 100 to provide the user with real-time information related to the status of the firing of handle assembly 100.

The trocar assembly 270 is axially and rotationally fixed within outer tube 206 of adapter assembly 200. With reference to FIG. 6, adapter assembly 200 includes a support block 292 fixedly disposed within outer tube 206. The strain gauge housing 320 is disposed between the support block 292 and a connector sleeve 290. The reload 400 is removably coupled to the connector sleeve 290.

In operation, strain gauge 408b of adapter assembly 200 measures and monitors the retraction of trocar member 274, which passes through the strain gauge 408b. The strain gauge 408b of adapter assembly 200 also measures and monitors ejection of the staples 423 from the reload 400, since the first and second flexible bands 255a, 255b also pass through the strain gauge 408b. During clamping, stapling and cutting, a reaction force is exerted on anvil assembly 500 and the reload 400, which is communicated to support block 29, which then communicates the reaction force to a strain sensor of the strain gauge 408b.

Strain sensor of strain gauge 408b may be any device configured to measure strain (a dimensionless quantity) on an object that it is adhered to (e.g., support block 292), such that, as the object deforms, a metallic foil of the strain sensor is also deformed, causing an electrical resistance thereof to change, which change in resistance is then used to calculate loads experienced by trocar assembly 270. Strain gauge 408b provides a closed-loop feedback to a firing/clamping load exhibited by first, second and third force/rotation transmitting/converting assemblies.

Strain sensor of strain gauge 408b then communicates signals to main controller circuit board 142. Graphics are then displayed on display 146 of power-pack core assembly 106 of handle assembly 100 to provide the user with real-time information related to the status of the firing of handle assembly 100. Strain gauge 408b is also electrically connected to the electrical connector 312 (FIG. 3) via proximal and distal harness assemblies 314, 316.

For further details regarding the construction and operation of the circular stapler and its components, reference may be made to International Application Publication No. PCT/US2019/040440, filed on Jul. 3, 2019, the entire contents of which being incorporated by reference herein.

During operation, the anvil assembly 500 (already positioned by surgeon) is attached to the trocar member 274 and the user begins the clamping process on the tissue interposed between reload 400 and the anvil assembly 500 by pressing on the bottom of the toggle control button 30. During clamping, the anvil assembly 500 is retracted toward the reload 400 until reaching a preset, fully clamped position, namely a position of the anvil assembly 500 at which the tissue is fully clamped between the anvil assembly 500 and the reload 400. The preset, fully clamped position varies for each of the different types of reloads (e.g., the distance is about 29 mm for 25 mm reloads). While clamping, the strain gauge 408b continuously provides measurements to the main controller 147 on the force imparted on the trocar member 274 as it moves the anvil assembly 500 to clamp tissue between the anvil assembly 500 and the reload 400.

The user commences a surgical procedure by positioning the adapter assembly 200, including the trocar member 274 and the anvil assembly 510, within the colorectal or upper gastrointestinal region. The user presses the toggle control button 30 to extend the trocar member 274 until it pierces tissue. After extension of the trocar member 274, the anvil assembly 510 that was previously positioned by surgeon is attached to the trocar member 274 and the user begins the clamping process on the tissue interposed between reload 400 and the anvil assembly 510 by pressing on the bottom portion of the toggle control button 30. Once clamping is successfully completed, the user initiates the stapling sequence.

To initiate stapling sequence, the user presses one of the safety buttons 36 of the power handle 101, which acts as a safety and arms the toggle control button 30, allowing it to commence stapling. Upon activation of the safety button 36, a rotation verification calibration check is performed. The display 146 transitions to the stapling sequence display, which includes a circle illustrating an animated view of a circular anastomosis, a progress bar, and a staple icon. The stapling sequence screen is displayed until user initiates the stapling sequence, exits the stapling sequence, or unclamps.

To commence the stapling sequence, the user presses down on the toggle control button 30, which moves the second rotation transmitting assembly 250 to convert rotation to linear motion and to eject and form staples from circular reload 400. In particular, during the firing sequence, the second motor 152 advances the driver 434 using the second rotation transmitting assembly 250. The force imparted on the second rotation transmitting assembly 250 is monitored by the strain gauge 408b. The process is deemed complete once the second rotation transmitting assembly 250 reaches a hard stop corresponding to a force threshold and detected by the strain gauge 408b. This indicates that the staples have been successfully ejected and deformed against the anvil assembly 510.

Figure 8:
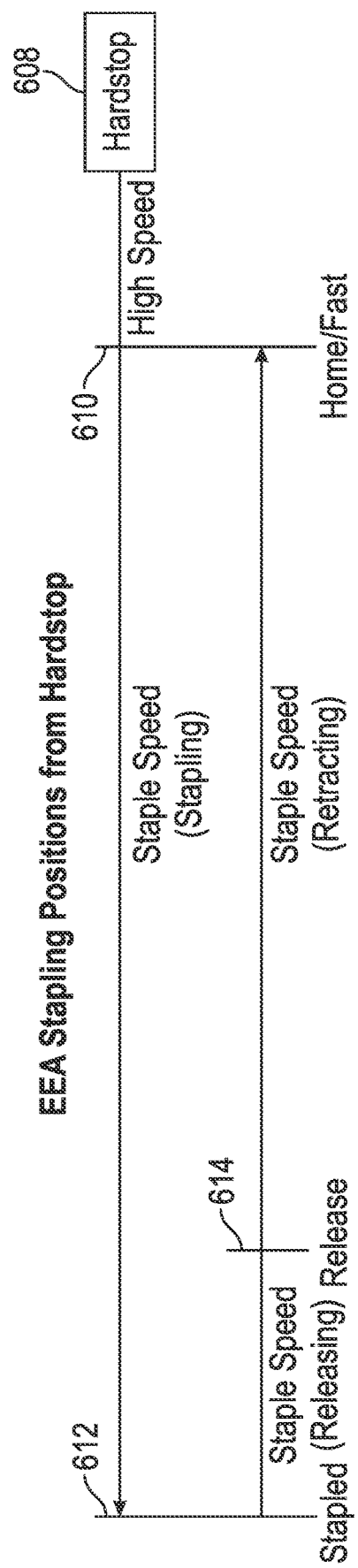
FIG. 8 is a schematic diagram illustrating travel distance and speed of a staple driver during a stapling sequence performed by the surgical instrument of FIG. 1 according to an embodiment of the present disclosure.

With reference to FIG. 8, which schematically illustrates the travel distance and speed of the motor 152 as it advances the driver 434 within the reload 400. The staple driver is initially advanced from a first distance 608 (e.g., hardstop) at a first speed for a first segment from the first distance 608 to a second distance 610 (e.g., base position). From the second distance 610, the driver 434 is advanced at a second speed, slower than the first speed, until it reaches a third distance 612 (e.g., target staple position), to eject the staples.

After reaching the second distance 610, the motor 152 is operated at the second, slower speed to eject the staples from the reload 400. During the second segment, as the staples are ejected from the reload 400 to staple tissue, the main controller 147 continually monitors the strain measured by the strain gauge 408b and determines whether the force corresponding to the measured strain is between a minimum stapling force and a maximum stapling force. The stapling force range may be stored in the storage device 402 of the reload 400 and used by the main controller 147 during the stapling sequence. Determination whether the measured force is below the minimum stapling force is used to verify that the staples are present in the reload 400. In addition, a low force may be also indicative of a failure of the strain gauge 408b. If the measured force is below the minimum stapling force, then the main controller 147 signals the motor 152 to retract the driver 434 to the second distance 610. The main controller 147 also displays a sequence on the display 146 instructing the user the steps to exit stapling sequence and retract the anvil assembly 510. After removing the anvil assembly 510, the user may replace the circular adapter assembly 200 and the reload 400 and restart the stapling process.

If the measured force is above the maximum stapling force, which may be about 500 lbs., the main controller 147 stops the motor 152 and displays a sequence on the display 146 instructing the user the steps to exit the stapling sequence. However, the user may still continue the stapling process without force limit detection by pressing on toggle control button 30.

The main controller 147 determines that the stapling process is completed successfully, if the motor 152 reached a third distance 612 associated with stapled tissue and during this movement the measured strain was within the minimum and maximum stapling force limits. Thereafter, the motor 152 retracts the driver 434 to a fourth distance 614 to release pressure on the tissue and subsequently to the second distance 610 prior to starting the cutting sequence.

The main controller 147 is also configured to account for band compression of outer flexible band assembly 255 during the stapling process which may result in a non-linear relationship between motor position as determined by the main controller 147 and position of components of the circular adapter assembly 200. The main controller 147 is configured to resolve the discrepancy between the calculated position of the motor 152 and the actual position of the components of the circular adapter assembly 200 using a second order mapping of force changes that result in the discrepancies. The force changes are based on the strain measurements from the strain gauge 408b. In particular, the main controller 147 maintains a count of lost turns by the motors 152, namely, turns that did not result in movement of the components of the circular adapter assembly 200, e.g., due to compression of the first and second flexible bands 255a, 255b, based on the force imparted on the components of the circular adapter assembly 200. The main controller 147 accumulates the total lost turns each time the imparted force changes by a predetermined amount, e.g., about 5 lbs. The motor position is then adjusted by the total accumulated lost-turns value to determine whether the target position has been attained.

The main controller 147 is configured to execute a staple variable backlash algorithm, which accounts for and compensates for mechanical losses of the stapling transmission assembly 250, namely, due to compression of the first and second flexible bands 255a and 255b during the stapling process. Mechanical losses in the stapling transmission assembly 250 result in a non-linear relationship between rotational position of the motor 152 and linear position of the stapling transmission assembly 250. The main controller 147 is configured to calculate a distance traveled by the stapling transmission assembly 250 by counting revolutions or other indicators of the motor 152 as measured by an encoder. The discrepancy between the rotational position of the motor 152, which is used to determine the calculated linear position, and the actual linear position of the stapling transmission assembly 250, is resolved using a second order mapping based on force changes as measured by the strain gauge 408b. Mapping may be expressed by a formula (I):

$$(I) y = ax^2 + bx + c$$

In formula (I), y is a number of lost turns and x is a force measured by the strain gauge 408b. As used herein, the term "lost turn" denotes a turn of the motor 152, which does not result in movement of the stapling transmission assembly 250.

Figure 9:
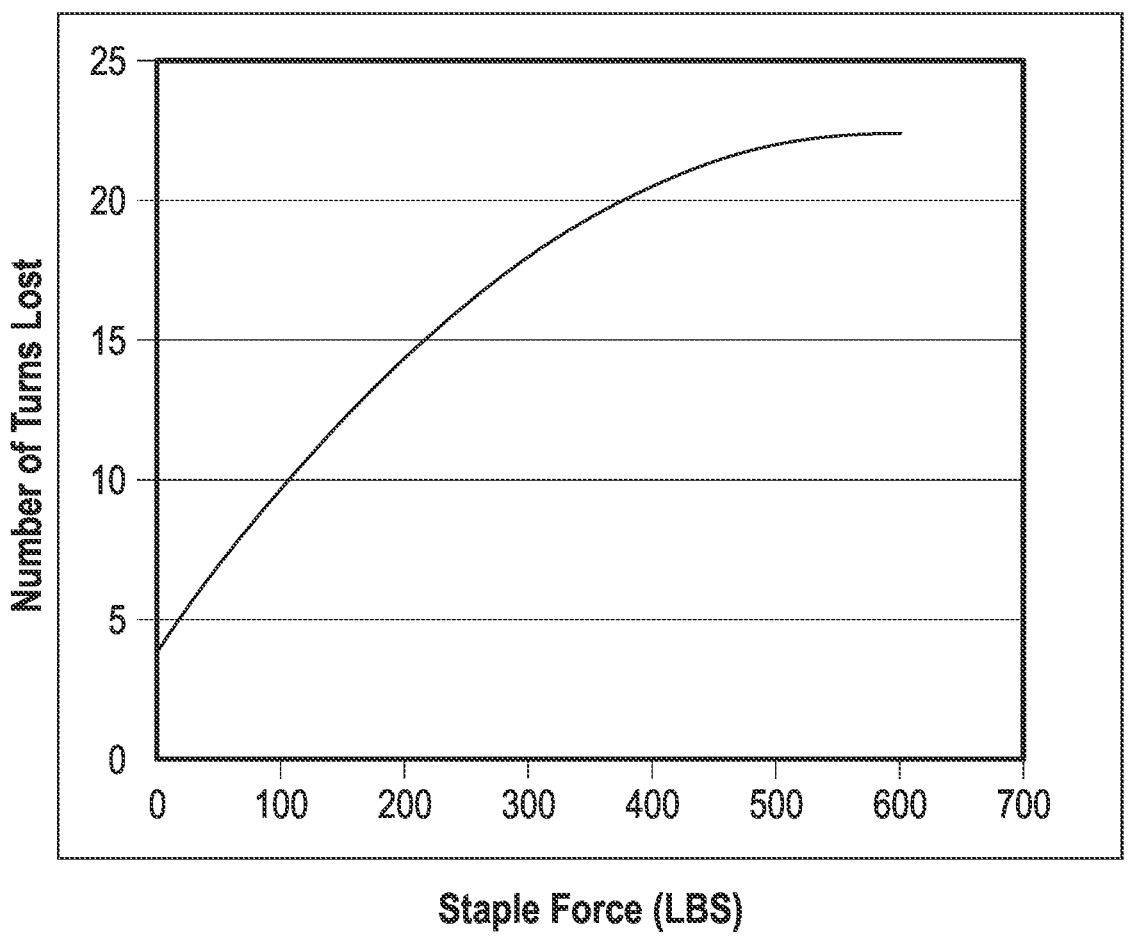
FIG. 9 is a plot of lost turns of motor and force during the stapling sequence performed by the surgical instrument of FIG. 1 according to an embodiment of the present disclosure.
Figure 10:
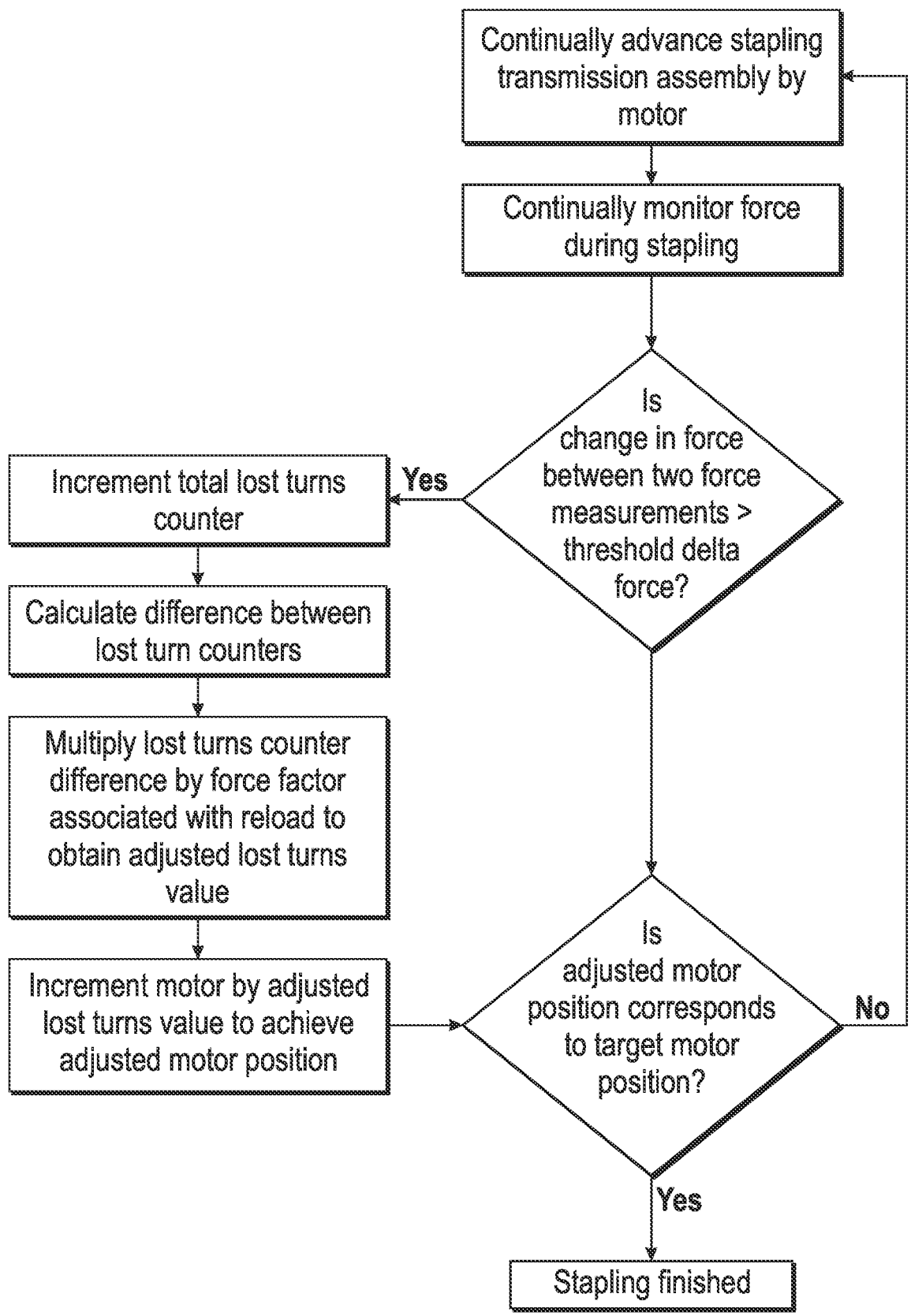
FIG. 10 is a method for controlling the surgical instrument of FIG. 1 during the stapling sequence according to an embodiment of the present disclosure.

Formula (I) is shown as a plot 80 in FIG. 9. The a and b coefficients determine the shape of the plot 80 and c coefficient represents the fixed backlash coming off the first distance 608 (e.g., hardstop). The coefficients a, b, and c are derived by performing a functional test, which includes performing a stapling procedure with the adapter assembly 200, while counting number of turns of the motor 152 and measuring the force through the strain gauge 408b. The functional test may be performed on the adapter assembly 200 during any time prior to its use, e.g., during manufacturing. The turn counts and the force measures are used to derive the coefficients, which are stored in the storage device 310 of the adapter assembly 200. The a, b, and c coefficients are read from the storage device 310 during initialization.

With reference to FIG. 9, which shows a staple variable backlash algorithm, during stapling, as the motor 152 advances the stapling transmission assembly 250, the main controller 147 continually monitors the force measured by the strain gauge 408b. The main controller 147 compares measured change in force between two force measurements for each sampling period, which may be about 1 millisecond, to a threshold delta force. The main controller 147 then accumulates, i.e., increments a counter, total lost turns each time the measured force changes more than the threshold delta force. The force at the beginning and end of the period is indexed to the lost-turns axis (vertical axis of plot 80). The difference in lost-turns between the number of lost turns at the current force and the number of lost turns at the previous force, is then multiplied by the force factor, read by the main controller 147 from the storage device 402 of the reload 400, and added to the accumulated lost-turns to obtain adjusted lost turns value. At each adjustment period, which may be about 1 millisecond, the position of the motor 152 is adjusted by the adjusted lost turns value and the main controller 147 determines if the target position is attained.

After adjustment of the motor 152, the main controller 147 checks whether the compensated motor position corresponding to the actual mechanical position of the stapling transmission assembly 250, is at, beyond, or within a tolerance distance the target motor position. If the compensated position corresponds to the target motor position, the staple stroke is considered complete and the motor movement is terminated.

In the event of a strain gauge error, e.g., failure of the strain gauge 408b, force cannot be used to adjust for mechanical discrepancies. The main controller 147 utilizes a default staple stroke, which is determined by combining the staple target position with the compensation from the staple backlash algorithm at a specific force of the reload 400.

The target staple position (i.e., third distance 612) is determined from a base position (i.e., second distance 610), which in turn is referenced from a calibration position and an offset stored in the storage device 402 of the reload 400. The storage device 402 also stores other values including rotation compensation or variable clamping compensation values that are added to the stapling distance. The base position may be set at a default value, e.g., about 0.225 inches, for all reloads 400.

Addition of the rotation compensation value is dependent on the clamp force at the start of the stapling process. If the measured clamp force is less than force threshold and the main controller 147 has been determined that the motor 152 has not been rotated, the target staple position, staple high speed position, and staple default position are adjusted to compensate for the change in mechanical position of the anvil assembly 510.

Addition of the variable clamping compensation values depends on the position of anvil assembly 510 in relation to the clamp gap target position when the powered surgical stapler 1 begins the stapling process. The target staple position (i.e., third distance 612) and the base position (i.e., second distance 610) are adjusted by the difference between the clamp position and the clamp gap target position to maintain the same distance.

When the powered circular stapler starts to staple and cut, a controller of the power handle monitors the force from a strain gauge disposed in the adapter assembly. Using the coefficients that were stored in the storage device of the adapter assembly by the final functional tester, the controller calculates the stroke losses in real time. The controller then adds additional motor ticks (i.e., revolutions) in order to compensate for the stroke lost between a distal end of the transmission assembly engaging the reload and a proximal end of the transmission assembly coupled to a motor of the power handle. Since the controller monitors the strain gauge in real time, the controller continuously adjusts the motors output until a distal pusher of the transmission assembly achieves the target stroke. After the stapling sequence is completed, the user presses the toggle control button 30 to commence the cutting sequence to cut the stapled and compressed tissue and form the anastomosis.

The staple variable backlash algorithm according to the present disclosure provides consistent stapling results regardless of the adapter, power handle and reload combination. The disclosed powered circular stapler 1 ensures properly formed staples across all tissue types and tissue thicknesses. This ensures intended device performance giving the best result for the patient and the user.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical device comprising:
   a power source;
   a motor coupled to the power source;
   a controller operably coupled to the motor;
   a memory storing a force factor corresponding to the surgical device;
   an adapter assembly comprising a stapling transmission assembly movable by the motor;
   a reload configured to selectively couple to a distal portion of the adapter assembly, the reload including a plurality of staples ejectable from the reload by the stapling transmission assembly;
   an anvil assembly selectively couplable to the distal portion of the adapter assembly, the anvil assembly being movable relative to the reload; and
   a force sensor communicatively coupled to the controller and configured to output measurement data corresponding to an imparted force on the stapling transmission assembly;

wherein, during motion of the stapling transmission assembly, the controller is configured to:
  determine a change in imparted force on the stapling transmission assembly based on the measurement data from the force sensor;
  increment a lost turns counter for the motor when the change in imparted force exceeds a threshold force value;
  determine an adjusted lost turns value by applying the force factor to the lost turns counter;
  control the motor, based on the adjusted lost turns value, to move the stapling transmission assembly to eject the plurality of staples.

2. The surgical device according to claim 1, wherein the stapling transmission assembly includes a pair of opposing flexible bands that deflect in response to compression resulting in lost turns of the motor.

3. The surgical device according to claim 1, further comprising an encoder coupled to the motor.

4. The surgical device according to claim 3, wherein the controller is further configured to determine a distance traveled by the stapling transmission assembly based on output from the encoder.

5. The surgical device according to claim 3, wherein the force sensor comprises a strain gauge assembly configured to measure the imparted force.

6. The surgical device according to claim 1, further comprising a set of coefficients stored in the memory and corresponding to the surgical device, wherein the controller is further configured to determine a compensation factor by applying the set of coefficients to a non-linear mapping formula relating to a number of lost turns by the motor.

7. The surgical device according to claim 6, wherein the non-linear mapping formula comprises a second order equation defined by the coefficients.

8. The surgical device according to claim 6, wherein the controller is further configured to determine a staple stroke by applying the compensation factor to a predetermined staple target position.

9. The surgical device according to claim 8, wherein the controller is further configured to control the motor to move the stapling transmission assembly to eject the plurality of staples with the determined staple stroke.

10. A surgical device comprising:
  a power source;
  a motor coupled to the power source;
  a controller operably coupled to the motor;
  a memory storing a set of coefficients corresponding to the surgical device;
  an adapter assembly comprising a stapling transmission assembly movable by the motor;
  a reload configured to selectively couple to a distal portion of the adapter assembly, the reload including a plurality of staples ejectable from the reload by the stapling transmission assembly;
  an anvil assembly selectively couplable to the distal portion of the adapter assembly, the anvil assembly being movable relative to the reload; and
  wherein, during motion of the stapling transmission assembly, the controller is configured to:
    determine a compensation factor by applying the set of coefficients to a mapping formula relating to a number of lost turns of the motor;
    determine a staple stroke by applying the compensation factor to a predetermined staple target position;
    control the motor to move the stapling transmission assembly to eject the plurality of staples with the determined staple stroke.

11. The surgical device according to claim 10, further comprising an encoder coupled to the motor, and wherein the controller is further configured to determine a distance traveled by the stapling transmission assembly based on output from the encoder.

12. The surgical device according to claim 11, further comprising a strain gauge assembly configured to measure force imparted on at least one of the stapling transmission assembly or the adapter assembly.

13. The surgical device according to claim 12, wherein the controller is further configured to determine a change in imparted force, and to perform a comparison of the change in imparted force with a threshold force.

14. The surgical device according to claim 13, wherein the controller is further configured to increment a lost turns counter based on the comparison.

15. The surgical device according to claim 14, further comprising a force factor stored in the memory and corresponding to the surgical device.

16. The surgical device according to claim 15, wherein the controller is further configured to multiply the lost turns counter by the force factor to determine an adjusted lost turns value.

17. The surgical device according to claim 16, wherein the controller is further configured to increment the motor by the adjusted lost turns value.

18. The surgical device according to claim 15, wherein the mapping formula comprises a second order equation defined by the coefficients.

19. The surgical device according to claim 10, wherein the reload and the anvil assembly are circular.

* * * * *